(12) United States Patent
Na et al.

(10) Patent No.: US 7,867,257 B2
(45) Date of Patent: Jan. 11, 2011

(54) POLY-AXIAL BONE SCREW MATING SEAT

(75) Inventors: Sean Joo Na, San Diego, CA (US); Jude V. Paganelli, San Diego, CA (US); Jason Yim, Solana Beach, CA (US); Brian Scott Bowman, Encinitas, CA (US)

(73) Assignee: Synthes USA, LLC, West Chester, PA (US)

( * ) Notice: Subject to any disclaimer, the term of this patent is extended or adjusted under 35 U.S.C. 154(b) by 600 days.

(21) Appl. No.: 11/550,280

(22) Filed: Oct. 17, 2006

(65) Prior Publication Data
US 2007/0233080 A1 Oct. 4, 2007

Related U.S. Application Data

(60) Provisional application No. 60/784,220, filed on Mar. 20, 2006.

(51) Int. Cl.
| | | |
|---|---|---|
| A61B 17/70 | (2006.01) | |
| A61B 17/04 | (2006.01) | |
| A61B 17/86 | (2006.01) | |
| A61F 2/08 | (2006.01) | |

(52) U.S. Cl. .................. 606/266; 606/305; 606/313
(58) Field of Classification Search ......... 606/246–276, 606/300–321
See application file for complete search history.

(56) References Cited

U.S. PATENT DOCUMENTS

| | | | |
|---|---|---|---|
| 2002/0032443 A1* | 3/2002 | Sherman et al. | 606/61 |
| 2005/0080415 A1 | 4/2005 | Keyer et al. | 606/61 |
| 2005/0187548 A1 | 8/2005 | Butler et al. | |
| 2005/0203516 A1* | 9/2005 | Biedermann et al. | 606/61 |
| 2005/0277927 A1 | 12/2005 | Guenther et al. | |

OTHER PUBLICATIONS

International Search Report for PCT/US2007/06537 dated Dec. 4, 2007.

* cited by examiner

*Primary Examiner*—Eduardo C Robert
*Assistant Examiner*—Christina Negrelli
(74) *Attorney, Agent, or Firm*—Stroock & Stroock & Lavan, LLP

(57) ABSTRACT

The present invention is directed a poly-axial bone securing system including a bone securing member and a coupling element. The coupling element includes an opening to permit the bone securing member to pass therethrough and a seat for contacting a head portion of the bone securing member. The opening including a discrete number of contact surfaces or points for engaging the head portion of the bone securing member so that discrete frictional or gripping forces may be generated at interface points of each contact surface or point.

11 Claims, 4 Drawing Sheets

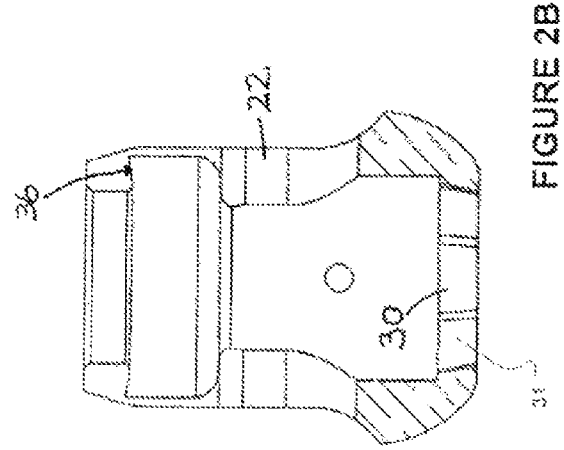
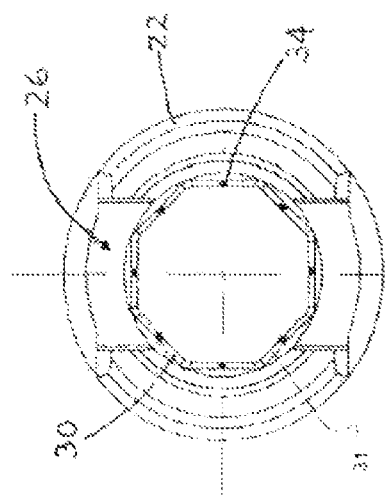
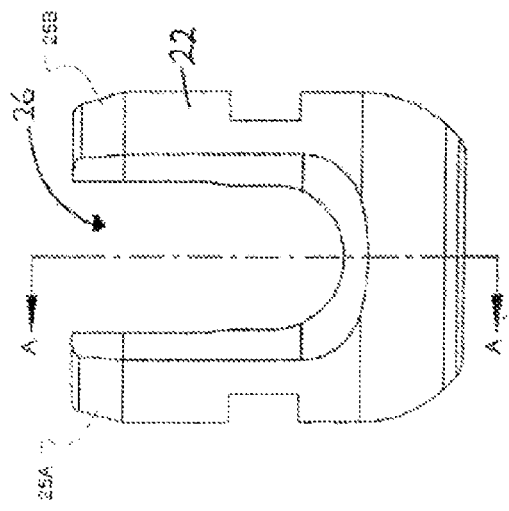

POLY-AXIAL BONE SCREW MATING SEAT

RELATED APPLICATIONS

This Application is a Non-Provisional of Provisional (35 USC 119(e)) application 60/784,220 filed on Mar. 20, 2006, the entireties of which are incorporated by reference herein.

TECHNICAL FIELD

The present invention relates generally to poly-axial bone screws and, more particularly, to poly-axial bone screws having improved gripping action between a screw head and a coupling element seat of the bone screw.

BACKGROUND ART

Bone securing systems may be provided to couple a bone stabilization rod or element to a bone securing member. In some systems a coupling member may be provided between the bone stabilization rod an bone securing member. The coupling member or element may include an interface between a portion of the bone securing member and the rod.

BRIEF DESCRIPTION OF THE DRAWINGS

FIG. 2A illustrates a perspective view of the coupling element, in accordance with one embodiment of the invention.

FIG. 2B illustrates a cross-sectional side view of the coupling element of FIG. 2A.

FIG. 2C illustrates a cross-sectional top view of the coupling element of FIG. 2A.

DETAILED DESCRIPTION

Figure 1C:
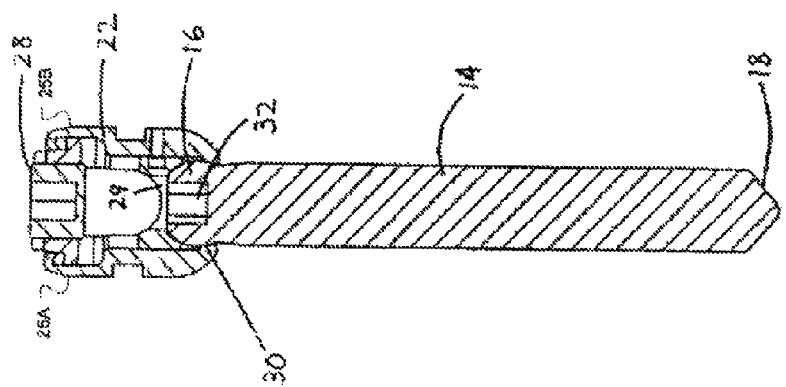
FIG. 1C illustrates a cross-sectional view of the poly-axial bone securing system of FIG. 1B.
Figure 1B:
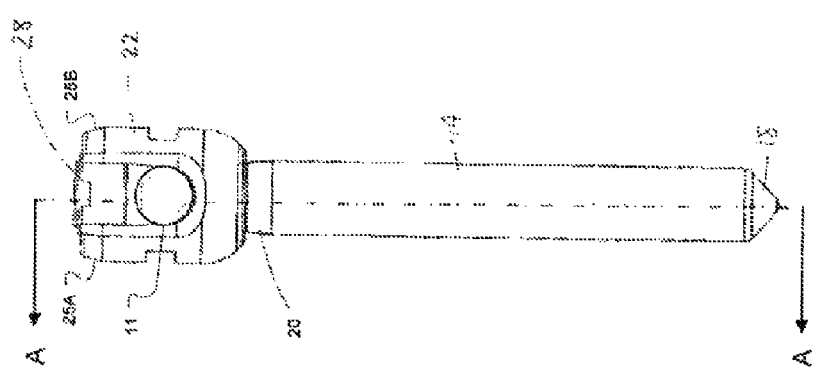
FIGS. 1A and 1B illustrate perspective view of a poly-axial bone securing system before and after assembly of the components of the system, in accordance with one embodiment of the invention.
Figure 1A:
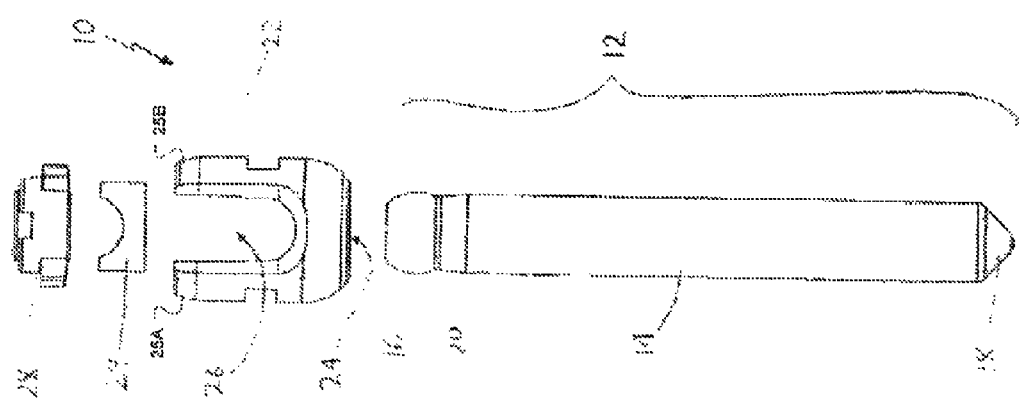

FIG. 1A illustrates an exploded view of a poly-axial bone securing system 10, in accordance with an embodiment of the invention. The poly-axial bone securing system 10 includes a bone securing member 12, rod to bone securing member coupling element 22, saddle member 29, and mating cap 28. In an embodiment, the bone securing member 12 has a threaded shaft portion 14 (threads not shown), a head portion 16, a tip 18, and a neck portion 20. The tip 18 may be configured to penetrate a patient's bone and be located at the distal end of the threaded shaft portion 14 opposite the bone securing member head 16. In an embodiment the bone securing member 12 may be a pedicle screw.

A neck portion 20 may be located between the screw head 16 and the threaded shaft 14. In one embodiment, the width of the neck portion 20 is narrower than the width of the threaded shaft 14, to enable increased poly-axial motion of the coupling element 22 when engaged with the bone securing member head 16. The coupling element 22 includes an opening 24 at a bottom surface configured to permit the bone securing tip 18 and the threaded shaft 14 to pass through. In an embodiment, the bone securing member head 16 may have a curved underside. The head 16 curved underside may engage a coupling member 22 seat 30 (FIG. 1C). The coupling element 22 may includes a side groove or channel 26 formed by two arms 25A, 25B for receiving a bone stabilization rod 11 (FIG. 1B) therein.

The bone securing system 10 may further include a mating cap 28 including a snap cap with set screw, interlocking cap, or a lock cap with set screw positioned therein. In an embodiment the mating cap 28 may lock a rod 11 within the coupling element 22 groove 26 by transferring a downward force from the rod 11, saddle member 29, securing member 12 head 16, and coupling element 22 seat 30. In an embodiment the saddle 29 may rest within the channel 26 on top of the bone securing member 12 head 16 and assist with holding the system 10 together after installation. The saddle 29 may have a bottom surface configured to rest on securing member 12 head 16 top surface and a top surface inwardly curved to matingly receive a cylindrical rod 11.

In an embodiment, the saddle 29 may act as an intermediate structure to facilitate an even distribution of load forces onto the bone securing member 12 head 16 top surface, the load forces created by the mating cap 28 being tightened onto a rod 11. The coupling head 22 includes a seat 30 to provide gripping and holding power between the coupling member 22 and the bone securing member 12 head 16 to limit any post-installation shifting of the bone securing member 12 with respect to the coupling element 22.

FIG. 1B illustrates a perspective view of an assembled poly-axial bone securing system of FIG. 1A. In an embodiment the bone securing member 12, after insertion into the coupling element 22 via the opening 24 may be driven into a bone (to be secured), such as a spinal pedicle via known techniques. The bone securing member 12 head 16 may include a Hex, Phillips, or other tool mating opening 32 (FIG. 1C). The securing member 12 may driven into bone up to the shoulder 20 to permit poly-axial articulation between the coupling member 22 and bone securing member 12 head 16 prior to mating cap 28 lock down. A rod 11 may be inserted into the channel 26 after the bone securing member 12 is installed in a bone.

The rod 11 and coupling element 22 may be adjusted into a desired relationship to the bone securing member 12 until the mating cap 28 is locked against the rod 11. FIG. 1C is a cross-sectional side view of the bone securing system 10 shown in FIG. 1B, taken along lines A-A. In an embodiment, the bone securing member head 16 underside may engage and rest upon a coupling element 12 seat 30. The seat 30 may define the opening 24 shape.

FIG. 2A is a perspective side view of the coupling element 22, in accordance with an embodiment of the invention. FIG. 2B is a cross-sectional side view of the coupling element 22 of FIG. 2A, taken along lines A-A and FIG. 2C is a cross-sectional top view of the coupling element 22 of FIGS. 2A and 2B. The coupling element 22 includes a multi-faceted 31 seat 30 that provides a discrete number of contact surfaces or points 34 for engaging the bone securing member 12 head 16 underside.

The coupling element 22 may also include a lip 36 for engaging a flange or protruding portion of the mating cap 28 to fixably couple the rod 11, coupling element 22, and bone securing member 12 together. As shown in FIG. 2C, the multi-faceted 31 seat 30 may be configured as a polygon including an octagon having eight distinct side surfaces or facets 31. When a bone securing member head 16 is seated within a multi-faceted seat 30 and pressed against the seat 30 via a mating cap 28 discrete frictional or gripping forces may be generated primarily at the interface points 34 indicated by the dots near the center of each side or facet 34 of the polygon-shaped seat 30.

The seat 30 may provide increased gripping forces between the bone securing member 12 head 16 and the coupling element 22 by providing a discrete number of contact points. In an embodiment when a bone securing member 12 head 16 is pressed into a seat 30, the primary contacts between the head 16 and the seat 30 are focused at or near the points 34. The multi-faceted 31 seat 30 may provide improved gripping action between the coupling element 22 and the bone securing member 12 head 16 due to the discrete number of contacts 34, reaction load, and head 16 deformation at the seat interface 30. The seat interface 30 may deform at each contact point 34 when a mating cap 38 is located into place due to pressure or stress at points 34. In an embodiment the seat 30 discrete contact points 34 may significantly increase the force per area between the coupling element 22 and securing member 12.

Figure 3B:
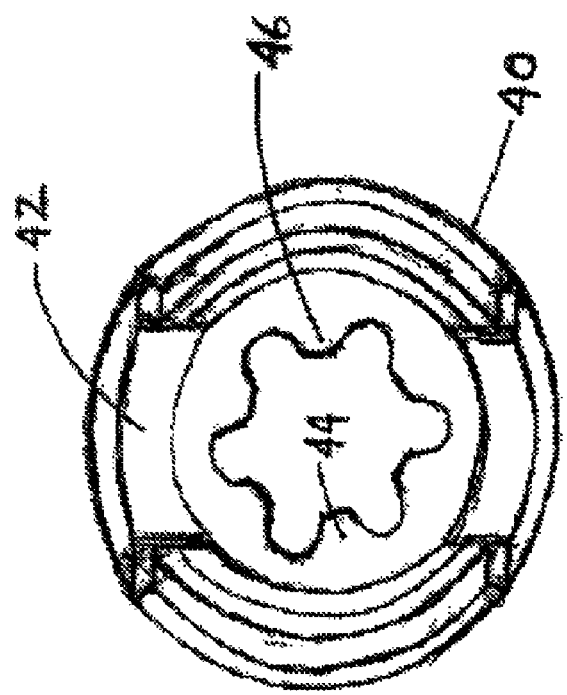
FIG. 3B illustrates a cross-sectional top view of the coupling element of FIG. 3A.
Figure 3A:
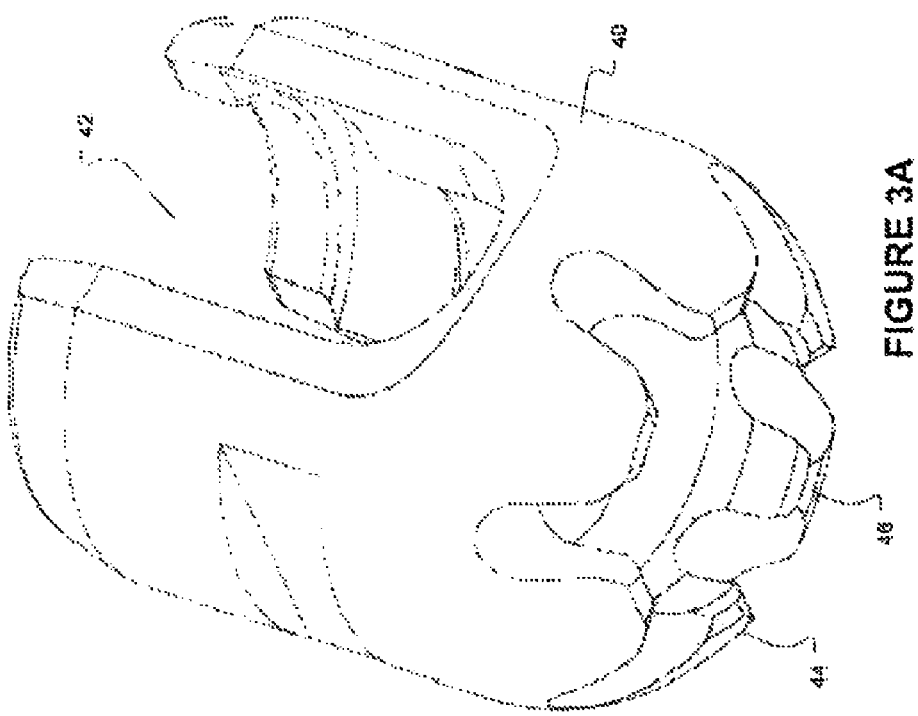
FIG. 3A illustrates a perspective view of another coupling element, in accordance with an embodiment of the invention.

FIG. 3A is a perspective view of another coupling element 40 in accordance with an embodiment of the invention. The coupling element 40 includes a channel 42 for receiving a rod (not shown) therein and a seat 44 having a discrete number of prongs 46. Each prong 46 may curve inwardly at a bottom portion of the coupling element 40. FIG. 3B is a cross-section top view of the coupling element 40. When a bone securing member 12 head 16 is seated on and pressed against the seat 44, it may engage the discrete number of prongs 46. In an embodiment the interior surface of the prongs 46 form the seat 44 and provide increased frictional force between the bone securing member 12 head 16 and the seat 44 in accordance with the principles discussed above with respect to coupling element 22.

The coupling element 40 may also provide increased flexibility and the ability to dynamically distribute loads across the seating surface due to the discrete number of prongs 46. The coupling element 40 may withstand and handle external forces reliably and not shift relative to the bone securing member 12 in the presence of external forces. In addition to prongs 46 may provide flexibility between the coupling element 40 and bone securing member 12 head 16 so loads may be distributed more evenly across the prongs 46.

Figure 4B:
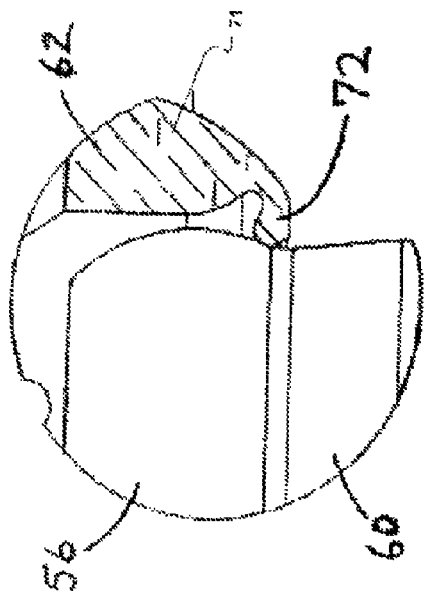
FIG. 4B illustrates a magnified view of the interface between the bone securing member head and a flexible J-shaped seat of the coupling element of FIG. 4A.
Figure 4A:
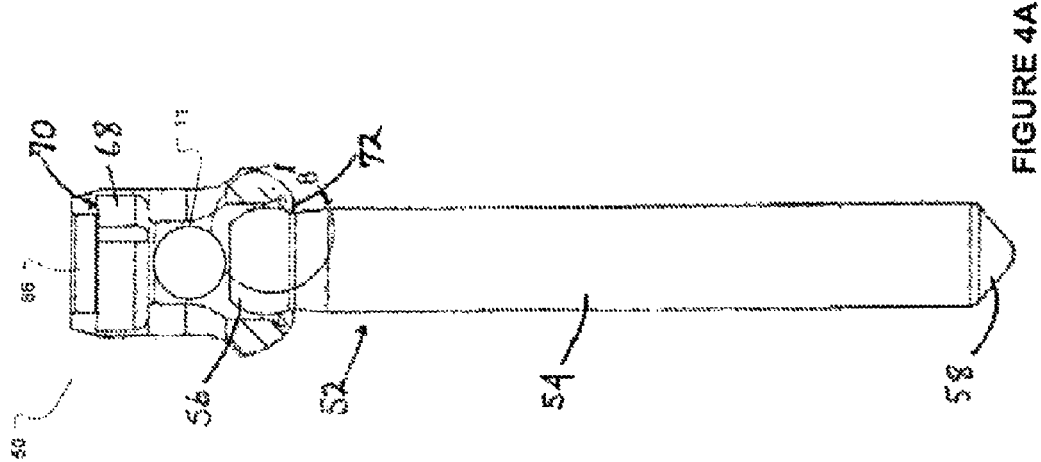
FIG. 4A illustrates a cross-sectional side view of the poly-axial bone securing system.

FIG. 4A is a cross-sectional view of a bone securing system 50 in accordance with an embodiment of the invention and FIG. 4B is an enlarged view of a section of the system 50. The bone securing system 50 includes a bone securing member 52 having a threaded shaft 54, a neck portion 60, a tip 58, and a spherical-shaped screw head 56. In an embodiment, the neck portion 60 is narrower than the threaded shaft 54 to allow increased poly-axial articulating motion between the coupling element 62 and bone securing member 52. The coupling head 62 may include a U-shaped channel 64 for receiving a bone stabilization rod 11 therein.

The system 50 may include a mating cap 68 (such as a snap cap) configured to be received and locked within a correspondingly shaped chamber 66 of the coupling element 62. The chamber 66 may include a ledge 70 configured to lock the mating cap 68 within the chamber 66. As shown in FIG. 4B, the coupling element 62 may include a circular J-shaped seat 71 having a J-shaped lip 72. The J-shaped seat 71 may be configured to flexibly hod the bone securing member 52 head 56 within the coupling element 62. The J-shaped seating surface lip 72 may provide greater ability to withstand and distribute loads between the seating surface 71 and the head 56, thus being less prone to shifting or breaking due to external forces. In an embodiment the seat 72 may be segmented into a discrete number of J-shaped lips 72 similar to prongs 46 shown in FIG. 3A.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus the following claims are hereby incorporated into the Detailed Description, with each claim standing on its own as a separate embodiment.

The invention claimed is:

1. A polyaxial bone securing system comprising:
    a bone securing member including a threaded shaft portion and a head portion;
    a coupling element including a rod receiving channel for receiving a longitudinal spinal rod, an upper end defining an upper opening, a lower end defining a lower opening, a bore extending from the upper opening to the lower opening, a seat adjacent the lower opening, the lower opening enabling the threaded shaft portion of the bone securing member to pass through;
    a saddle member disposed within the bore of the coupling element, the saddle member being located between the longitudinal spinal rod when inserted in the rod-receiving channel and the head portion of the bone securing member; and
    a mating cap for operatively engaging the coupling element for securing the longitudinal spinal rod and the bone securing member with respect to the coupling element;
    wherein the lower opening includes a discrete number of non-contiguous radially expandable contact elements, each contact element radially expanding against the head portion of the bone securing member to secure a position of the bone securing member with respect to the coupling element.

2. The polyaxial bone securing system of claim 1, wherein at least one of the radially expandable contact elements is deformable.

3. The polyaxial bone securing system of claim 1, wherein at least one of the radially expandable contact elements is flexible.

4. The polyaxial bone securing system of claim 1, wherein each contact element has a contact point for engaging the head portion of the bone securing element.

5. The polyaxial bone securing system of claim 1, wherein at least one of the radially expandable contact elements includes a prong.

6. A polyaxial bone securing system comprising:
 a bone securing member including a threaded shaft portion and a head portion; and
 a coupling element including a rod receiving channel for receiving a longitudinal spinal rod, an upper end defining an upper opening, a lower end defining a lower opening, a bore extending from the upper opening to the lower opening, a seat adjacent the lower opening, the having a lower opening for enabling the threaded shaft portion of the bone securing member to pass through;
 a saddle member disposed within the bore of the coupling element, the saddle member being located between the longitudinal spinal rod when inserted in the rod-receiving channel and the head portion of the bone securing member; and
 a mating cap for operatively engaging the coupling element for securing the longitudinal spinal rod and the bone securing member with respect to the coupling element;
 wherein the lower opening includes a plurality of radially expandable, flexibly deformable contact elements, each contact element capable of flexibly engaging the head portion of the bone securing member to secure a position of the bone securing member with respect to the coupling element; and
 wherein the position of the bone securing member is fixed with respect to the coupling element via the radially expansion of the contact elements against the head portion of the bone securing member and without an outer member disposed about the coupling element.

7. The polyaxial bone securing system of claim 6, wherein each of the flexibly deformable contact elements include a plurality of discrete sub-elements capable of flexibly engaging the head portion of the bone securing member.

8. The polyaxial bone securing system of claim 6, wherein each of the flexibly deformable contact elements include a flexibly deformable lip capable of flexibly engaging the head portion of the bone securing member.

9. A polyaxial bone securing system comprising:
 a bone securing member including a threaded shaft portion and a head portion; and
 a coupling element including a rod receiving channel for receiving a longitudinal spinal rod, an upper end defining an upper opening, a lower end defining a lower opening, a bore extending from the upper opening to the lower opening, a seat adjacent the lower opening, the lower opening enabling the threaded shaft portion of the bone securing member to pass through;
 a saddle member disposed within the bore of the coupling element, the saddle member being located between the longitudinal spinal rod when inserted in the rod-receiving channel and the head portion of the bone securing member; and
 a mating cap for operatively engaging the coupling element for securing the longitudinal spinal rod and the bone securing member with respect to the coupling element;
 wherein the lower opening includes a plurality of radially expandable, flexibly deformable contact elements, each contact element capable of flexibly engaging the head portion of the bone securing member to secure a position of the bone securing member with respect to the coupling element; and
 wherein the fixing of the bone securing member with respect to the coupling element consists essentially of the radially expansion of the contact elements against the head portion of the bone securing member.

10. The polyaxial bone securing system of claim 9, wherein each of the flexibly deformable contact elements include a plurality of discrete sub-elements capable of flexibly engaging the head portion of the bone securing member.

11. The polyaxial bone securing system of claim 9, wherein each of the flexibly deformable contact elements include a flexibly deformable lip capable of flexibly engaging the head portion of the bone securing member.

* * * * *

UNITED STATES PATENT AND TRADEMARK OFFICE
CERTIFICATE OF CORRECTION

| | | |
|---|---|---|
| PATENT NO. | : 7,867,257 B2 | Page 1 of 1 |
| APPLICATION NO. | : 11/550280 | |
| DATED | : January 11, 2011 | |
| INVENTOR(S) | : Sean Joo Na et al. | |

It is certified that error appears in the above-identified patent and that said Letters Patent is hereby corrected as shown below:

Title page, item (73) Assignee: delete "Synthes USA, LLC, West Chester, PA (US)" and substitute therefor -- N SPINE, INC., San Diego, CA (US) --

Signed and Sealed this
Twenty-sixth Day of July, 2011

David J. Kappos
*Director of the United States Patent and Trademark Office*